US006339168B1

(12) United States Patent
Klatt et al.

(10) Patent No.: US 6,339,168 B1
(45) Date of Patent: Jan. 15, 2002

(54) COMPOSITION COMPRISING STABILIZED PHOSPHORUS COMPOUNDS

(75) Inventors: Martin Klatt, Mannheim; Christa Hackl, Osnabrück; Günter Scholz, Lemförde, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/547,484

(22) Filed: Apr. 12, 2000

(30) Foreign Application Priority Data

Apr. 15, 1999 (DE) .......................... 199 17 070

(51) Int. Cl.⁷ .................................. C07F 9/02
(52) U.S. Cl. .................. 558/71; 252/387; 252/388
(58) Field of Search ...................... 508/257; 558/71

(56) References Cited

U.S. PATENT DOCUMENTS

| 4,012,464 A |   | 3/1977  | Buckles et al. ............... 558/71 |
|-------------|---|---------|----------------------------------------|
| 4,496,495 A | * | 1/1985  | Caspari et al. ............... 558/71 |
| 5,342,978 A | * | 8/1994  | Enlow et al. .................. 558/71 |
| 5,468,895 A |   | 11/1995 | Mahood ........................ 558/71 |
| 5,534,645 A | * | 7/1996  | Quotschalla et al. .......... 558/71 |
| 5,674,927 A | * | 10/1997 | Mahood ........................ 558/71 |
| 5,840,954 A | * | 11/1998 | Quotschalla et al. .......... 558/71 |

FOREIGN PATENT DOCUMENTS

| EP | A-0 143 464 A2 | 6/1985  |
| EP | A-0 167 969 A2 | 1/1986  |
| RU | 2067598        | 10/1996 |

OTHER PUBLICATIONS

Chemical Abstract XP–002144404—6001, Columbus, Ohio, US; vol. 126 Feb. 6, 1997; No. 22.

* cited by examiner

*Primary Examiner*—Ellen M. McAvoy
(74) *Attorney, Agent, or Firm*—Fernando A. Borrego; Mary K. Cameron

(57) ABSTRACT

A composition comprising at least
 a phosphorus compound and
 a stabilizer compound having one of the formulae I to IV
can be used for increasing the shelf life or reducing metal corrosion.

8 Claims, No Drawings

COMPOSITION COMPRISING STABILIZED PHOSPHORUS COMPOUNDS

The present invention relates to a composition comprising stabilized phosphorus compounds and the use of this composition for increasing the shelf life or reducing metal corrosion.

The use of phosphorus compounds is usually associated with the problem that firstly they only have a short shelf life and secondly that they are so aggressive that they corrode metals. The short shelf life and the high tendency to cause corrosion of metals of the preferably organic phosphorus compounds leads to them being difficult to transport over long distances, particularly when they are handled industrially. Furthermore, the storage of phosphorus compounds for a prolonged period of time is associated with considerable technical difficulties. However, the economically satisfactory use of organic phosphorus compounds in industry generally makes it necessary to transport them in containers of an economically acceptable size, for example in railroad tank cars. Furthermore, phosphorus compounds are usually processed in continuous processes with other materials to give new products, in which case the phosphorus compounds have to be fed in over a long period and therefore have to be stored appropriately.

It is an object of the present invention to provide compositions comprising phosphorus compounds which have both a long shelf life and a low tendency to corrode metals.

We have found that this object is achieved by a composition comprising at least one phosphorus compound and at least one stabilizer compound having one of the formulae I to IV:

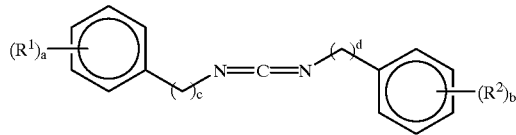
(I)

where $R^1$, $R^2$ are each, independently of one another, a hydrogen atom, a $C_1$–$C_{10}$-alkyl radical, a $C_6$–$C_{12}$-aryl radical, a $C_7$–$C_{13}$-aralkyl radical or a $C_7$–$C_{13}$-alkylaryl radical, a, b are, independently of one another, from 1 to 5, c, d are, independently of one another, from 0 to 10;

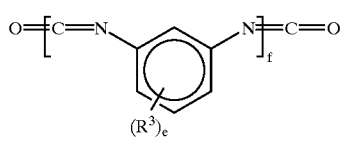
(II)

where $R^3$ is a hydrogen atom, a $C_1$–$C_{10}$-alkyl radical, a $C_6$–$C_{12}$-aryl radical, a $C_7$–$C_{13}$-aralkyl radical or a $C_7$–$C_{13}$-alkylaryl radical, e is from 1 to 4,
f is from 1 to 100;

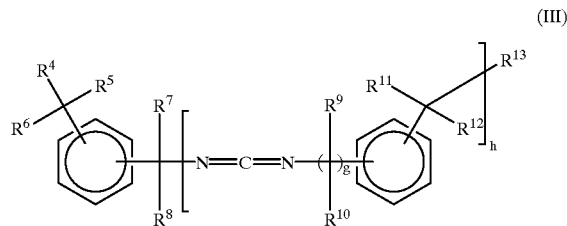
(III)

where $R^4$, $R^{13}$ are, independently of one another, NCO or NHCOOR', where R' is an alkyl polyether glycol or a $C_1$–$C_{20}$-alcohol, $R^5$, $R^6$, $R^7$, $R^8$, $R^9$, $R^{10}$, $R^{11}$, $R^{12}$ are each, independently of one another, a hydrogen atom, a $C_1$–$C_{10}$-alkyl radical, a $C_6$–$C_{12}$-aryl radical, a $C_7$–$C_{13}$-aralkyl radical or a $C_7$–$C_{13}$-alkylaryl radical, g is from 0 to 5,
h is from 1 to 100;

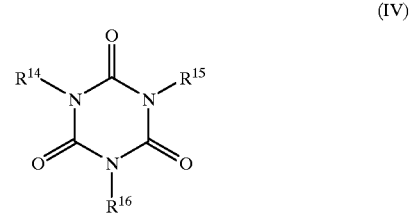
(IV)

where $R^{14}$, $R^{15}$, $R^{16}$ are each, independently of one another, a hydrogen atom or

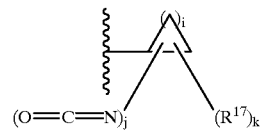

where $R^{17}$ is a hydrogen atom, a $C_1$–$C_{10}$-alkyl radical, a $C_6$–$C_{12}$-aryl radical, a $C_7$–$C_{13}$-aralkyl radical or a $C_7$–$C_{13}$-alkylaryl radical, i is from 2 to 8,
j is from 1 to i–k
k is from 0 to j, where j+k≦i, denotes the C—N bond to the nitrogen heterocycle of the formula IV, or $(CH_2)_1$—N=C=O, where 1 is from 1 to 20.

According to the present invention, $R^1$ and $R^2$ are preferably each, independently of one another, a $C_1$–$C_{10}$-alkyl radical, particularly preferably a $C_1$–$C_4$-alkyl radical and more preferably a $C_3$-alkyl radical. Among these, a 2-propyl radical is particularly preferred.

The integral variables a and b are preferably each, independently of one another, 1, 2, 3 or 4 and particularly preferably 2. When a and b are each 2, the corresponding radicals $R^1$ and $R^2$ are each located on the carbon atom next to the carbon at which the NCN group is attached to the benzene ring.

Among the $C_6$–$C_{12}$-aryl radicals, $C_6$–$C_{10}$-aryl radicals are preferred and $C_6$–$C_8$-aryl radicals are particularly preferred according to the present invention. Among the abovementioned aryl radicals, phenyl and naphthyl radicals are very particularly preferred. Preferred aralkyl radicals having preferably from 7 to 14 carbon atoms are tolyl, xylyl, tert-butylphenyl and di-tert-butylphenyl. As alkylaryl radical, preference is given to one having from 7 to 14 carbon atoms, and benzyl is particularly preferred.

According to the present invention, the variables c and d are preferably, independently of one another, 0, 1, 2, 3, 4 or 5 and particularly preferably 0, 1 or 2. Further preference is given to the case where c and d are each 0.

As regards the preferred meanings of the radical $R^3$, what has been said above about the radicals $R^1$ and $R^2$ applies.

The integral variable e is preferably 1, 2 or 3 and particularly preferably 3. When the variable e is 3, it is preferred that the radicals R3 are each bound to the carbon atoms of the benzene ring which are next to those to which a nitrogen is bound.

The integral variable f is preferably in the range from 1 to 50 and particularly preferably in the range from 1 to 20.

R' is preferably derived from a $C_1-C_{10}$-alcohol and particularly preferably from a $C_2-C_5$-alcohol. Among these alcohols, preference is in turn given to ethanol, n-propanol, isopropanol, n-butanol, isobutanol, tert-butanol, n-pentanol and isopentanol, with ethanol being particularly preferred.

If R' is an alkyl polyether glycol, preference is given to $C_1-C_{10}$-alkyl polyether glycols and particular preference is given to $C_1-C_5$-alkyl polyether glycols. Among these, preference is in turn given to methyl, ethyl, propyl and isopropyl polyether glycols and particular preference is given to methyl polyether glycols. The alkyl polyether glycols preferably have a molecular weight in the range from 1000 to 1,000,000 g/mol, preferably from 1500 to 100,000 g/mol and particularly preferably from 2000 to 10,000 g/mol.

As regards the preferred meanings of $R^5$, $R^6$, $R^7$, $R^8$, $R^9$, $R^{10}$, $R^{11}$ and $R^{12}$, what has been said above regarding $R^1$ and $R^2$ applies, except that a methyl radical rather than the 2-propyl radical is particularly preferred.

The integral variable g is preferably 0, 1, 2, 3 and particularly preferably 0. The variable h is preferably 1, 2, 3, 4, 5, 6, 7, 8, 9 or 10 and particularly preferably 2, 3, 4, 5 or 6.

The radicals $R^{14}$, $R^{15}$ and $R^{16}$ are preferably not hydrogen atoms.

As regards $R^{17}$, what has been said regarding $R^5$ to $R^{12}$ likewise applies. The integral variable i is preferably 3, 4 or 5 and particularly preferably 5, so that a cyclohexyl ring is formed with the carbon via which the cyclic radical is bound to the nitrogen of the heterocycle. Preference is also given to the variable i being 1.

In the case of a cyclohexyl ring being formed, the integral variable k is preferably 4. In this case, it is in turn preferred that in each case two of the four radicals $R^{17}$ are bound to a carbon of the cyclohexyl ring and are separated from the further carbon likewise bearing two radicals $R^{17}$ by a carbon atom located in between.

A preferred embodiment of the composition of the present invention contains from 0.01 to 20% by weight, preferably from 0.01 to 5% by weight, in particular from 0.05 to 2% by weight, based on the composition, of at least one stabilizer compound.

In another preferred embodiment, the composition of the present invention contains from 99.99 to 80% by weight, based on the composition, of at least one phosphorus compound.

Phosphorus compounds preferred according to the present invention have from 6 to 120, preferably from 6 to 80 and particularly preferably from 8 to 40, carbon atoms.

All phosphorus compounds known to a person skilled in the art are possible for the composition of the present invention. Among these, particular preference is given to organic phosphorus compounds which are used industrially or have a short shelf life or a high tendency to cause corrosion or both. Among these organic phosphorus compounds, particular preference is given to those of the formula (V).

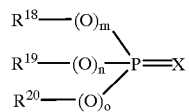

(V)

where $R^{18}$, $R^{19}$ and $R^{20}$ are each, independently of one another, an alkyl radical, an aryl radical, an alkylaryl radical, an arylalkyl radical or a cycloalkyl radical having from 7 to 40 carbon atoms or a cycloalkyl radical having from 5 to 40 carbon atoms;

x is a sulfur or oxygen atom, preferably an oxygen atom;

m, n, o are, independently of one another, 0 or 1, preferably 0.

In one embodiment of the phosphorus compound of the formula V, it is preferred that two of the variables m, n and o are 0 and 1.

Examples of phosphine oxides as phosphorus compounds are triphenylphosphine oxide, tritolylphosphine oxide, tris-nonylphenylphosphine oxide, tricyclohexylphosphine oxide, tris(n-butyl)phosphine oxide, tris(n-hexyl)phosphine oxide, tris(n-octyl)phosphine oxide, tris(cyanoethyl)phosphine oxide, benzylbis(cyclohexyl)phosphine oxide, benzylbisphenylphosphine oxide, phenylbis(n-hexyl)phosphine oxide. Preference is also given to oxidized reaction products of phosphine with aldehydes, in particular of t-butylphosphine with glyoxal. Particular preference is given to using triphenylphosphine oxide, tricyclohexylphosphine oxide and tris(n-octyl)phosphine oxide.

Likewise suitable as phosphorus compound are triphenylphosphine sulfide and its derivatives analogous to the above-described phosphine oxides, and also triphenyl phosphate.

Phosphorus compounds in the oxidation state ±0 are elemental phosphorus. Possibilities are red and black phosphorus. Preference is given to red phosphorus.

Phosphorus compounds having the oxidation state +1 are, for example, hypophosphites. Examples are organic hypophosphites such as cellulose hypophosphite esters, esters of hypophosphorous acid with diols, e.g. of 1,10-dodecanediol. Substituted phosphinic acids and their anhydrides, e.g. diphenylphosphinic acid, can also be used. Further suitable compounds are di-p-tolylphosphinic acid, dicresylphosphinic anhydride. However, compounds such as hydroquinone bis(diphenylphosphinate), ethylene glycol bis(diphenylphosphinate), propylene glycol bis(diphenylphosphinate), etc., are also possibilities. Other suitable compounds are aryl (alkyl)phosphinamides, e.g. diphenylphosphinic acid dimethylamide, and sulfonamidoaryl(alkyl)phosphinic acid derivatives, e.g. p-tolylsulfonamidodiphenylphosphinic acid. Preference is given to using hydroquinone bis(diphenylphosphinate) and ethylene glycol bis(diphenylphosphinate).

Phosphorus compounds having the oxidation state +3 are derived from phosphorous acid. Suitable compounds are cyclic phosphonates derived from pentaerythritol, neopentyl glycol or catechol, as shown in the formula VI

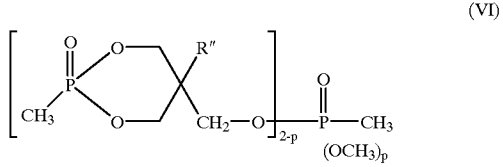
(VI)

where R″ is a $C_1$–$C_4$-alkyl radical, preferably a methyl radical, and p=0 or 1 (Amgardâ P45 from Albright & Wilson).

Phosphorus in the oxidation state +3 is also present in triaryl(alkyl) phosphites, e.g. triphenyl phosphite, tris(4-decylphenyl) phosphite, tris(2,4-di-tert-butyl-phenyl) phosphite, trisnonylphenyl phosphite (for example Irgaphos® TNPP from Ciba Geigy AG) or phenyldodecyl phosphite, etc. However, diphosphites such as propylene glycol 1,2-bis(diphosphite), or cyclic phosphites derived from pentaerythritol, neopentyl glycol or catechol are also possibilities.

As phosphorus compounds having the oxidation state +3, particular preference is given to methyl neopentyl glycol phosphonate and phosphite and also dimethyl pentaerythritol diphosphonate and phosphite.

Suitable phosphorus compounds having the oxidation state +4 are, in particular, hypodiphosphates, e.g. tetraphenyl hypodiphosphate or bisneopentyl hypodiphosphate.

Particularly suitable phosphorus compounds having the oxidation state +5 are alkyl- and aryl-substituted phosphates. Examples are phenyl bisdodecyl phosphate, phenyl ethyl hydrogen phosphate, phenyl bis(3,5,5-trimethylhexyl) phosphate, ethyl diphenyl phosphate, 2-ethylhexyl di(tolyl) phosphate, diphenyl hydrogen phosphate, bis(2-ethylhexyl) p-tolyl phosphate, tritolyl phosphate, bis(2-ethylhexyl) phenyl phosphate, di(nonyl) phenyl phosphate, phenyl methyl hydrogen phosphate, di(dodecyl) p-tolyl phosphate, p-tolyl bis-(2,5,5-trimethylhexyl) phosphate and 2-ethylhexyl diphenyl phosphate. Phosphorus compounds in which each radical is an aryloxy radical are particularly useful. Very particularly suitable compounds are triphenyl phosphate and resorcinol bis(diphenyl phosphate) (RDP) and its ring-substituted derivatives of the formula VII

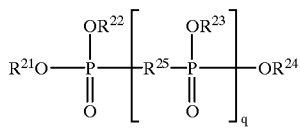
(VII)

where
$R^{21}$ to $R^{24}$ are each an aromatic radical having from 6 to 20 carbon atoms, preferably a phenyl radical, which may be substituted by alkyl groups having from 1 to 4 carbon atoms, preferably methyl,
$R^{25}$ is a divalent phenol radical, preferably

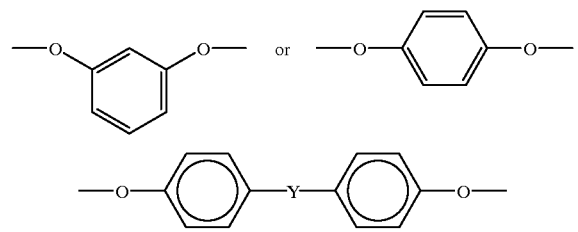

where Y is —$CH_2$—, C=O, S, $SO_2$, —$C(CH_3)_2$—, preferably —$C(CH_3)_2$—and q has an average value of from 0.1 to 100, preferably from 0.5 to 50, in particular from 0.8 to 10 and very particularly preferably from 1 to 5.

Particular preference is given to the phosphorus compound of the formula VIII

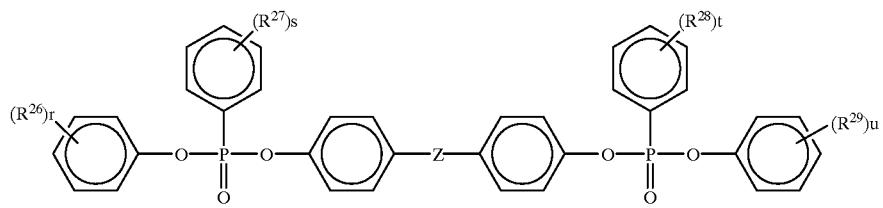

where
$R^{26}$, $R^{27}$, $R^{28}$, $R^{29}$ are each, independently of one another, a hydrogen atom or a $C_1$–$C6$-alkyl radical,
z is as defined above for the radical Y,
r,s,t,u are, independently of one another, 1, 2, 3, 4 or 5, with preference being given to 1 and the para-position of the corresponding radical relative to the phosphorus.

The RDP products obtainable commercially under the trade designations FyroflexR-RDP (Akzo Nobel) and CR 733-S (Daihachi) are, as a result of the production process, mixtures of about 85% of RDP with about 2.5% of triphenyl phosphate and about 12.5% of oligomeric components in which the degree of oligomerization is usually <10.

Furthermore, it is also possible to use cyclic phosphates as phosphorus compounds. Particularly suitable compounds of this type are diphenyl pentaerythritol diphosphate and phenyl neopentyl phosphate.

Apart from the abovementioned low molecular weight phosphorus compounds, oligomeric and polymeric phosphorus compounds are also possibilities.

Such polymeric, preferably halogen-free organic phosphorus compounds having phosphorus in the polymer chain are formed, for example, in the preparation of pentacyclic, unsaturated phosphine dihalides, as is described, for example, in DE-A 20 36 173. The molecular weight, measured by vapor pressure osmometry in dimethylformamide, of the polyphospholine oxides should be in the range from 500 to 7000, preferably in the range from 700 to 2000. Here, the phosphorus is in the oxidation state −1.

It is also possible to use inorganic coordination polymers of aryl(alkyl)phosphinic acids, e.g. poly-b-sodium(I)

methylphenylphosphinate, as phosphorus compounds. Their preparation is described in DE-A 31 40 520. The phosphorus is in the oxidation state +1.

Furthermore, such, preferably halogen-free, polymeric phosphorus compounds can be formed by reaction of a phosphonic acid chloride, e.g. phenylphosphonic, methylphosphonic, propylphosphonic, styrylphosphonic or vinylphosphonic dichloride, with bifunctional phenols, e.g. hydroquinone, resorcinol, 2,3,5-trimethylhydroquinone, bisphenol A or tetramethylbisphenol A.

Further, preferably halogen-free, polymeric phosphorus compounds which may be present in the compositions of the present invention are prepared by reaction of phosphorus oxide trichloride or phosphoric ester dichlorides with a mixture of monofunctional, bifunctional and trifunctional phenols and other hydroxyl-containing compounds (cf. Houben-Weyl-Müller, Thieme-Verlag Stuttgart, Organische Phosphorverbindungen, Part II (1963)). Polymeric phosphonates can also be prepared by transesterification reactions of phosphonic esters with bifunctional phenols (e.g. DE-A 29 25 208) or by reactions of phosphonic esters with diamines or diamides or hydrazides (cf. U.S. Pat. No. 4,403,075). However, the inorganic compound poly(ammonium phosphate) is also a possibility.

It is also possible to use oligomeric pentaerythrityl phosphites, phosphates and phosphonates as described in EP-B 8 486, e.g. Mobil Antiblazeâ 19 (registered trademark of Mobil Oil), as phosphorus compounds.

Furthermore, preference is given to a composition according to the present invention whose acid number after a period of from 1 to 100 days, preferably from 2 to 50 days and particularly preferably from 10 to 30 days, from the time at which the phosphorus compound is brought into contact with the stabilizer compound differs by not more than 20%, preferably not more than 15% and particularly preferably not more than 5%, from the acid number at the time at which the phosphorus compound and the stabilizer compound are brought into contact.

The phosphorus compound and the stabilizer compound and, if desired, other auxiliaries and additives which are customarily added can be brought into contact with one another by all methods generally known to those skilled in the art. However, mixing in tanks by means of moving mixers or mixing of the composition moving, for example, through a descending tube by means of a static mixer has been found to be useful.

The composition of the present invention or the stabilizer compound or at least two thereof are preferably used for increasing the shelf life of phosphorus compounds or for reducing the tendency of phosphorus compounds to corrode metals.

According to the present invention, the shelf life is determined by the change in the acid number over the storage time of the particular composition.

The shelf life is preferably such that over a period of 5 days, preferably 2 weeks and particularly preferably one month, the acid number changes by not more than 10%, preferably not more than 5% and particularly preferably not more than 1%, from the acid number at the beginning of the specified period.

The tendency to corrode metals is determined from a comparison of the corrosion caused by a particular compound with or without stabilizer compound under otherwise identical conditions over an equal period.

As commercial stabilizer compounds, Vestanat® 1890/100 from Hüls AG, Basonat® H/100 from BASF AG, Stabaxol® 1 from Rhein-Chemie GmbH, Stabaxol® p from Rhein Chemie GmbH and Elastostab® from Elastogran GmbH have been found to be particularly useful.

Stabilizer compounds which are particularly preferred according to the present invention comprise at least one of the compounds shown below by way of their structural formulae:

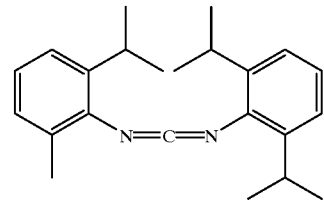

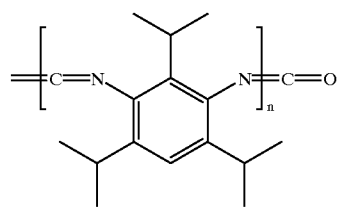

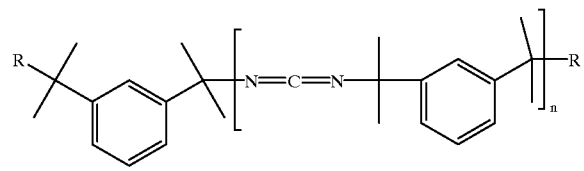

where R=NHCOOR', R'=methyl polyether glycol, R'=ethanol
R=NCO or reaction product Carbodiimide-free isocyanurates

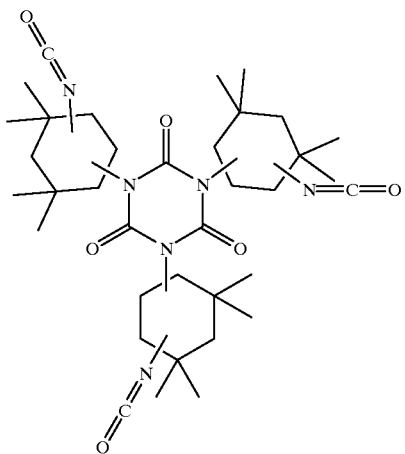

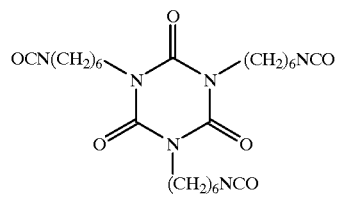

The invention is illustrated by the non-limiting examples below:

EXAMPLES

The components indicated below were mixed at room temperature in a customary mixing apparatus.

Component 1: Resorcinol bis(diphenyl phosphate)
Component 2: Elastostab® HO1
Component 3: Elastostab® HO2
Component 4: Vestanat® 1890/100
Component 5: Basonat® HI 100
Component 6: NCO-free reaction product of Elastostab® HO2 with ethanol

| Comp.   |        |       |       |       |       |       |        |
|---------|--------|-------|-------|-------|-------|-------|--------|
| 1       | 99     | 99    | 90    | 95    | 90    | 90    | 100    |
| 2       | 1      | 2     |       |       |       |       |        |
| 3       |        |       | 10    |       |       |       |        |
| 4       |        |       |       | 5     |       |       |        |
| 5       |        |       |       |       | 10    |       |        |
| 6       |        |       |       |       |       | 10    |        |
| AN (0)  | 0.13   | 0.13  | n.m.  | n.m.  | n.m.  | n.m.  | 0.13   |
| AN (7)  | 0.13   | 0.13  | n.m.  | n.m.  | n.m.  | n.m.  | 0.34   |
| AN (14) | 0.14   | 0.15  | n.m.  | n.m.  | n.m.  | n.m.  | 0.62   |
| AN (21) | 0.19   | 0.18  | n.m.  | n.m.  | n.m.  | n.m.  | 0.81   |
| Cu corr.| medium | weak  | weak  | none  | weak  | weak  | strong | n.m.: not measured
AN: acid number

As a measure of decomposition, the acid number was determined after storage at 80° C. for 0, 7, 14 and 21 days by dissolving in acetone, addition of a defined amount of 0.5 M KOH and titration. The unit is mg of KOH.

For examination of the Cu corrosion (Cu corr.), a drop of the sample was placed on a polished Cu sheet and stored at 160° C. for 7 days. The Cu sheet was then washed with acetone and the discoloration in the region of the sample was assessed visually.

We claim:

1. A composition comprising a phosphorus compound and at least one stabilizer compound having one of the formulae I to IV

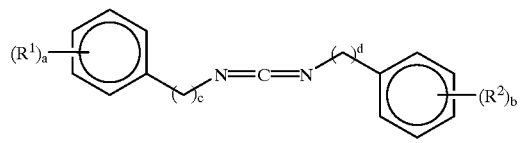
(I)

where $R^1$, $R^2$ are each, independently of one another, a hydrogen atom, a $C_1$–$C_{10}$-alkyl radical, a $C_6$–$C_{12}$-aryl radical, a $C_7$–$C_{13}$-aralkyl radical or a $C_7$–$C_{13}$-alkylaryl radical, a, b are, independently of one another, from 1 to 5, c, d are, independently of one another, from 0 to 10;

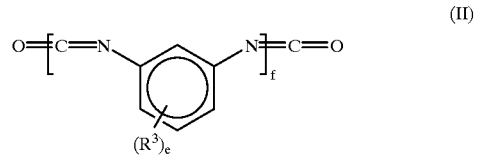
(II)

where $R^3$ is a hydrogen atom, a $C_1$–$C_{10}$-alkyl radical, a $C_6$–$C_{12}$-aryl radical, a $C_7$–$C_{13}$-aralkyl radical or a $C_7$–$C_{13}$-alkylaryl radical, e is from 1 to 4, f is from 1 to 100;

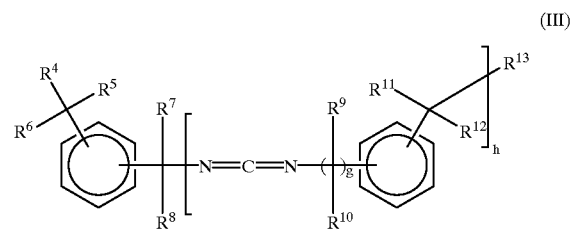
(III)

where $R^4$, $R^{13}$ are, independently of one another, NCO or NHCOOR', where R' is an alkyl polyether glycol or a $C_1$–$C_{20}$-alcohol, $R^5$, $R^6$, $R^7$, $R^8$, $R^9$, $R^{10}$, $R^{11}$, $R^{12}$ are each, independently of one another, a hydrogen atom, a $C_1$–$C_{10}$-alkyl radical, a $C_6$–$C_{12}$-aryl radical, a $C_7$–$C_{13}$-aralkyl radical or a $C_7$–$C_{13}$-alkylaryl radical, g is from 0 to 5, h is from 1 to 100;

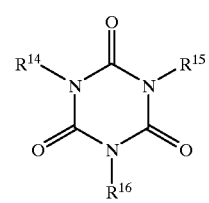
(IV)

where $R^{14}$, $R^{15}$, $R^{16}$ are each, independently of one another, a hydrogen atom or

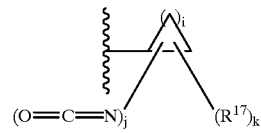

where $R^{17}$ is a hydrogen atom, a $C_1$–$C_{10}$-alkyl radical, a $C_6$–$C_{12}$-aryl radical, a $C_7$–$C_{13}$-aralkyl radical or a $C_7$–$C_{13}$-alkylaryl radical, i is from 2 to 8, j is from 1 to i–k k is from 0 to i–j, where j+k≦i, denotes the C-N bond to the nitrogen heterocycle of the formula IV,
or $(CH_2)_1-N=C=O$, where l is from 1 to 20.

2. A composition as claimed in claim 1 containing from 0.01 to 20% by weight, based on the composition, of said at least one stabilizer compound.

3. A composition as claimed in claim 1 containing from 99.99 to 80% by weight, based on the composition, of the phosphorus compound.

4. A composition as claimed in claim 1, wherein the phosphorus compound is a phosphorus compound having from 8 to 120 carbon atoms.

5. A composition as claimed in claim 4, wherein the phosphorus compound has the formula V

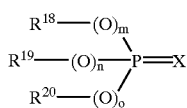 (V)

where
$R^{18}$, $R^{19}$, $R^{20}$ are each, independently of one another, an alkyl radical, an alkylaryl radical, an arylalkyl radical or a cycloalkyl radical having from 7 to 40 carbon atoms, or a cycloalkyl radical having from 4 to 40 carbon atoms, X is a sulfur or oxygen atom, m,n,o are, independently of one another, 0 or 1.

6. A composition as claimed in claim 1, wherein the phosphorus compound is selected from the group consisting of triphenylphosphine oxide, triphenylphosphine sulfide, triphenyl phosphate, resorcinol bis(diphenyl phosphate) and triphenylphosphine and mixtures thereof.

7. A composition as claimed in claim 1, whose acid number after a period of from 1 to 100 days from the time at which the phosphorus compound is brought into contact with the stabilizer compound differs by not more than 20% from the acid number at the time at which the phosphorus compound and the stabilizer compound are brought into contact.

8. Method of increasing the shelf life of phosphorus compounds or for reducing the tendency of phosphorus compounds to corrode metals, comprising adding a stabilizer compound as defined in claim 1 to the phosphorus compounds.

* * * * *